United States Patent [19]
Giordano et al.

[11] Patent Number: 5,362,871
[45] Date of Patent: * Nov. 8, 1994

[54] PROCESS FOR THE DIRECT AND REGIOSELECTIVE FUNCTIONALIZATION IN POSITION 2 OF PHENOTHIAZINE

[75] Inventors: Claudio Giordano, Monza; Maurizio Paiocchi; Paolo Cavalleri, both of Milan, all of Italy

[73] Assignee: Zambon Group S.p.A., Vicenza, Italy

[*] Notice: The portion of the term of this patent subsequent to Feb. 18, 2009 has been disclaimed.

[21] Appl. No.: 833,800

[22] Filed: Feb. 12, 1992

[30] Foreign Application Priority Data

Feb. 14, 1991 [IT] Italy ............................ MI91A000379

[51] Int. Cl.$^5$ ...................... C07D 279/20; C07B 45/06
[52] U.S. Cl. ........................................ 544/40; 544/35
[58] Field of Search ..................... 544/35, 40

[56] References Cited

U.S. PATENT DOCUMENTS

| | | | |
|---|---|---|---|
| 3,961,055 | 6/1976 | Baget | 260/243 A |
| 4,578,379 | 3/1986 | Cormier | 514/223 |
| 5,089,613 | 2/1992 | Meneghin | 544/35 |
| 5,109,134 | 4/1992 | Meneghin | 544/36 |

FOREIGN PATENT DOCUMENTS

| | | |
|---|---|---|
| 0451675 | 10/1991 | European Pat. Off. . |
| 0433841 | 6/1992 | European Pat. Off. . |
| 1314521 | 12/1962 | France . |

OTHER PUBLICATIONS

Merck Index, XI Ed., No. 9290, p. 1474 (Thioridazine) (1990).
Merck Index, XI Ed., No. 5813, p. 929 (Mesoridazine) (1990).
Merck Index, X Ed., No. 5847, p. 857 (Methiomeprazine) (1990).
Merck Index, XI Ed., No. 9241, p. 1467 (Thiethylperazine) (1990).
Chemical Abstracts-C.A. 81:15387c-Japanese Pat. Appln. No. 48-28761 (Yoshitomi Pharmaceutical K.K.) (1973).
Helvetica Chimica Acta, 41, 1061, 1958 Bourquin et al.
Saret, Heterocycles, vol. 26, No. 1, p. 239 (1987).
Clark J. Chem. Soc., Perkin Trans. II, 1103-1110 (1978).
Dahlbom Acta Chim. Scand. 7, 879-884 (1953).
Burmistrov Chemical Abstracts-C.A. 84:59346e-Zh. Org. Khim, 11, 2230 (1975).
Borquin Helvetica Chimica Acta, 41, 1072 (1958).

*Primary Examiner*—Mark L. Berch
*Attorney, Agent, or Firm*—Stevens, Davis, Miller & Mosher

[57] ABSTRACT

A process for the direct and regioselective functionalization of phenothiazine which allows one to introduce an SH group in position 2, said process comprising the sulfination or sulfonation of the phenothiazine N-protected with an alkoxycarbonyl, an alkylsulfonyl or an arylsulfonyl group, the reduction of the produce obtained to give the N-protected 2-mercapto-phenothiazine, and the deprotection of the nitrogen atom. The thus-obtained 2-mercapto-phenothiazine is an important intermediate for the preparation of pharmacological active compounds.

5 Claims, No Drawings

PROCESS FOR THE DIRECT AND REGIOSELECTIVE FUNCTIONALIZATION IN POSITION 2 OF PHENOTHIAZINE

The present invention relates to a process for the preparation of 2-mercapto-phenothiazine, which is a useful intermediate for the preparation of drugs.

2-Mercapto-phenothiazine of formula

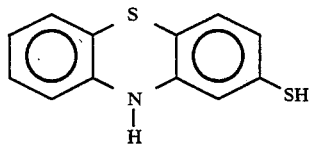
(I)

is a known intermediate for the preparation of compounds with pharmaceutical activity among which

- Thioridazine (Merck Index, XI Ed., No. 9290, page 1474)
- Mesoridazine (Merck Index, XI Ed., No. 5813, page 929)
- Methiomeprazine (Merck Index, X Ed., No. 5847, page 857)
- Thiethylperazine (Merck Index, XI Ed., No. 9241, page 1467) may be cited.

Compound I is also an intermediate for the synthesis of some of the compounds with contraceptive activity described in U.S. Pat. No. 4,578,379 (Univ. Georgia Res.) and for the synthesis of some of the compounds useful as stabilizers for hydrocarbons described in the Japanese patent application No. 48-28761 [Yoshitomi Pharmaceutical K.K.—(C.A. 81:15387c)].

Several processes for the preparation of the compound of formula I are known but, however, they often show negative features which make them not very suitable from an industrial point of view. Such negative features include a long synthesis which needs a high number of steps and the separation and purification of the intermediates, starting materials which are not available on the market or available only at high cost, reactants and catalysts of difficult industrial use, low yields or again the formation of by-products of difficult separation.

As an example of the several methods in the literature, the following may be cited: a three-steps synthesis starting from a condensation between 3-mercapto-aniline and 2-chloro-benzoic acid which provides compound I with the 4-mercapto isomer as an impurity (Helvetica Chimica Acta, 41, 1061, 1958) and the methods of preparation collected in Heterocycles, vol. 26, No. 1, page 239, (1987). In co-pending U.S. patent application Ser. No. 626,763 (filed on Dec. 13, 1990) (now U.S. Pat. No. 5,109,134) and Ser. No. 680,942 (filed on Apr. 5, 1991) (now U.S. Pat. No. 5,089,613) a process for the direct and regioselective functionalization in position 2 of phenothiazine by sulfination and by sulfonation respectively is described.

The starting compounds in these processes are phenothiazine N-protected by an acyl group of a $C_1$-$C_6$ aliphatic carboxylic acid or of benzoic acid, preferably, by a formyl, acetyl or benzoyl group. These processes are characterized by a high regioselectivity, however, in the functionalization step, N-deacylation may occur and a reprotection step is often necessary.

We have now found that the protection of phenothiazine with an alkoxycarbonyl, an alkylsulfonyl or an arylsulfonyl group allows to avoid any N-deprotection in the functionalization step while maintaining the high regioselectivity of the reaction.

In this connection, it is worth noting the process for the sulfonylation of unprotected phenothiazine described in French patent No. 1,314,521 (Chimiotechnic S.A.) which provides an unidentified disulfonyl derivative of phenothiazine.

It is the object of the present invention a process for the preparation of 2-mercapto-phenothiazine which comprises the direct functionalization of phenothiazine by regioselective introduction in position 2 of an SH group.

Such process comprises the reaction of an N-protected phenothiazine of formula

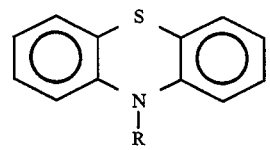
(II)

wherein R is a —COOR' or —$SO_2R''$ group in which R' is a $C_1$-$C_6$ alkyl and R'' is a $C_1$-$C_6$ alkyl or an optionally substituted phenyl or naphthyl;

with a sulfinating or sulfonating agent, in order to obtain a compound of formula III

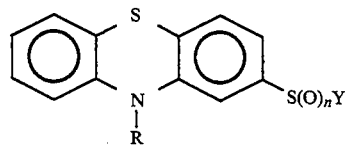
(III)

wherein
n is 2 or 3;
when n=3, Y is a hydrogen atom, an alkaline metal or a cation of an organic base and,
when n=2, Y has the same meanings or may also be a chlorine atom;
R has the above reported meanings;
its reduction to obtain the N-protected 2-mercapto-phenothiazine of formula IV

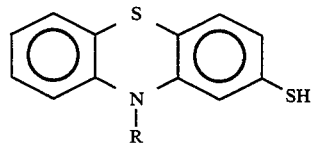
(IV)

wherein R has the above reported meanings; and the deprotection of the nitrogen atom to obtain 2-mercapto-phenothiazine of formula I.

A specific example of sulfinating agent is sulfur dioxide ($SO_2$) which is used in the presence of aluminum chloride ($AlCl_3$).

The sulfonating agent is selected among 96–98% sulfuric acid, sulfur trioxide, chlorosulfonic acid and oleum, chlorosulfonic acid being preferred.

The starting compound of the process is the N-protected phenothiazine of formula II.

Preferably an N-alkoxycarbonyl derivative of formula II (R=—COOR') is used in the process of the invention.

Still more preferred is the use of N-methoxycarbonyl-phenothiazine (R'=CH3) as starting compound of formula II.

The compounds of formula II are known. In particular, the N-alkoxycarbonyl derivatives (R=—COOR') can be prepared, for example, by treatment of phenothiazine-10-carbonyl chloride, a compound available on the market, with a suitable alkoxide [J. Chem. Soc., Perkin Trans. II, 1103–1110, (1978)] or by direct treatment of phenothiazine with a suitable alkoxycarbonyl chloride [Acta Chim. Scand. 7, 879–884, (1953)].

The sulfonyl derivatives II (R=—SO2R'') can be prepared for example, by direct treatment of phenothiazine with the corresponding chlorosulfonyl derivative [Zh. Org. Khim. 11, 2230, (1975)—C.A. 84:59346e].

The reaction of the compound of formula II with a sulfinating agent gives the compounds of formula III wherein n=2, Y=H.

The reaction of the compounds of formula II with a sulfonating agent gives, after work up of the reaction mixture, the compounds of formula III wherein n=3.

The preparation of the compounds of formula III wherein n=2 and Y=H is generally carried out with sulfur dioxide (SO2) and aluminum chloride (AlCl3) and, in particular, it can be carried out in the absence of a solvent or in the presence of an inert solvent.

The resultant N-protected phenothiazine-2-sulfinic acid is directly reduced and deprotected in order to obtain 2-mercapto-phenothiazine I.

The preparation of the compounds of formula III wherein n=3 and Y=H is carried out by using specific sulfonating agents such as, for example, 96–98% sulfuric acid, sulfur trioxide, chlorosulfonic acid and oleum.

In particular, the sulfonation reaction is carried out in the absence of a solvent or in the presence of an inert solvent selected among methylene chloride, 1,2-dichloroethane, sulfur dioxide, nitrobenzene, nitromethane, sulfuryl fluoride and acetic acid.

The compounds of formula III obtained from the above described functionalization reactions are preferably isolated as salts (Y=alkaline metal or cation of an organic base) by treatment with aqueous alkaline bases or with organic bases or with suitable salts such as, for example, alkaline salts or quaternary ammonium salts. Preferred examples of salts of the compounds of formula III are the salts with alkaline metals such as sodium or potassium or with lipophilic tertiary amines such as N,N-dimethyl-n.octylamine, tributylamine, tripentylamine, trihexylamine. Alternatively, the compounds of formula III wherein n=3 and Y=H can be isolated as such.

The compounds of formula III wherein Y=H, an alkaline metal or a cation of an organic base are reduced according to conventional techniques suitable to reduce the sulfur atom in order to yield the N-protected 2-mercapto-phenothiazine.

For example, the salts of formula III can be reduced with polysulfides according to known methods.

A method, which affords good results with low industrial cost, consists in carrying out the reduction with zinc in acid environment. In particular, in the process object of the invention the compounds of formula III in the form of acids as well as of salts are not isolated but directly reduced.

The treatment of the reduction mixture with bases such as aqueous sodium or potassium hydroxide gives the deprotected 2-mercapto-phenothiazine of formula I.

Alternatively, the deprotection reaction can be carried in the same salification environment of the compounds of formula III (Y=H) when the salifying agent is an aqueous alkaline base.

Preferably, the compounds of formula III wherein n=3 in the form of an acid or of a salt can be transformed into the corresponding sulfonyl chloride (Y=Cl) by reaction with thionyl chloride, generally in the presence of an inept organic solvent such as, for example, methylene chloride, toluene, 1,2-dichloroethane and of a catalytic amount of dimethylformamide. The reaction gives high yields (higher than 90%).

The reduction step of the resultant sulfonyl chloride to compound IV is preferably carried out with zinc in hydrochloric or sulfuric acid and, practically, it can be carried out by adding to the organic solution of the sulfonyl chloride (III, Y=Cl) the acid and, then, zinc.

The work up of the reduction mixture with aqueous alkaline bases and the subsequent acidification allow to obtain the compound of formula I.

A practical embodiment of the process object of the invention is the following.

The compounds of formula II are treated with aluminum chloride and sulfur dioxide to obtain the compounds of formula III wherein n=2 and Y=H.

The amount of aluminum chloride to be used is at least equimolar with respect to compound II even if an excess from 2 to 4 times in moles is preferably used.

The reaction is carried out with gaseous SO2. It is preferred to treat, at first, AlCl3 with SO2.

To the resultant complex, compound II is added as such or dissolved in an inert organic solvent.

Alternatively, gaseous SO2 is bubbled into a suspension of AlCl3 in an inert solvent.

Examples of suitable solvents are those usually used in the Friedel-Crafts reactions with AlCl3 such as for example CH2Cl2, CS2, CHCl2CHCl2, CH2ClCH2Cl.

The reaction mixture is kept under SO2 atmosphere and at a temperature from 0° to 100° C., preferably from room temperature to 70° C. At the end of the reaction, the resultant mixture is diluted with an organic solvent, for example CH2Cl2.

The reduction step is preferably carried out with zinc and hydrochloric acid and, practically, it can be carried out directly in the organic solution, obtained by dilution of the mixture resultant from the functionalization reaction, as well as after treatment of such a solution with acidic water in order to separate the aluminum salts. Alternatively, at the end of the Friedel-Crafts reaction the salt of the compounds of formula III (n=2) can be isolated by treatment, for example, with aqueous alkaline bases and by reduction according to the above described procedure.

In another practical embodiment, the process of the invention consists in the functionalization of the compound of formula II by using a sulfonating agent such as chlorosulfonic acid or 96% sulfuric acid.

When the sulfonating agent is chlorosulfonic acid, the amount to be used is preferably from 2 to 4 times in moles higher than that of the substrate and the reaction is carried out in the presence of an inert solvent such as, for example, methylene chloride and 1,2-dichloroethane.

When the sulfonating agent is sulfuric acid (96%) the preferred amount is from 4 to 20 times in moles higher than that of the substrate.

However, in both cases the sulfonation reaction is carried out at a temperature from −20° C. to 80° C., preferably from 15° C. to 40° C.

The compounds of formula III wherein n=3 are preferably transformed into the corresponding sulfonyl chloride (n=2, Y=Cl) with thionyl chloride, in the presence of an inert organic solvent and of catalytic amounts of dimethylformamide.

The resultant sulfonyl chloride is reduced with zinc in hydrochloric acid and then directly deprotected with aqueous alkaline bases.

The resultant compound I is useful for the preparation of known drugs.

For example, the compound of formula I can be methylated directly in the same reaction environment in order to obtain 2-methylthio-phenothiazine. This latter is a useful intermediate in the preparation of drugs such as, for example, Thioridazine [Helvetica Chimica Acta, 41, 1072, (1958)].

The methylation reaction is per se known and it is carried out with conventional methylating agents for industrial use such as dimethylsulfate and methyl chloride.

Clearly, the compound of formula I can be alkylated with an alkyl different from methyl (for example ethyl), by using suitable alkylating agents which depend on the alkyl to be introduced.

Accordingly, for example, 2-ethylthio-phenothiazine, an intermediate useful for the synthesis of thiethylperazine can be prepared [Helvetica Chimica Acta, 41, 1072, (1958)].

The most typical and innovating aspect of the present process is the functionalization step of phenothiazine II which affords compound III with good yield and with a practically complete regioselectivity of the attack in position 2.

In fact, the used reaction conditions allow to obtain a practically complete monosubstitution in position 2 of the phenothiazine ring. The presence of the 2,8-disubstituted by-product is limited to very small amounts (lower than 5%) and, therefore, it is practically absent or easily removable by known techniques.

The process object of the invention shows various advantages with respect to the processes of the prior art.

Such advantages, whose industrial usefulness is clear to the man of the art, can be summarized in the low cost of the starting materials, in their easy availability in industrial amounts, in the reduced number of steps (N-protection of phenothiazine, functionalization in position 2, reduction and deprotection) in the easy industrial application of the above steps, which allows also a one-pot synthesis, in the high regioselectivity of the process and in the remarkably higher global yield than that obtainable by the known methods.

In order to better illustrate the invention the following examples, which refer, in particular, to the preferred embodiments of the invention, are now given.

EXAMPLE 1

Preparation of N-methoxycarbonyl-phenothiazine-2-sulfonic acid sodium salt

Chlorosulfonic acid (45.5 g; 0.39 moles) was added dropwise, in about 10 minutes, to a mixture of N-methoxycarbonyl-phenothiazine (50 g; 0,194 moles) [prepared as described in Acta Chim. Scand. 7, 879–884, (1953)] in methylene chloride (75 ml) cooled at 15° C.

The mixture was heated to 25° C. and kept at this temperature and under stirring for 3 hours.

Then, the reaction mixture was poured into water and ice (250 g) and the phases were separated. A solution of sodium chloride (114 g) in water (300 ml) was added to the aqueous phase under stirring. After 1 hour at 20° C. the precipitate was filtered and washed with water (2×50 ml).

After drying under vacuum at 50° C. for 12 hours N-methoxycarbonyl-phenothiazine-2-sulfonic acid sodium salt having a 90% HPLC titre was obtained (50.3 g; 65% yield).

The crude compound was used in the subsequent step without further purification.

$^1$H-NMR (300 MHz, DMSO-d$_6$): δ (ppm): 3.75 (s, 3H); 7.22–7.85 (m, 7H).

EXAMPLE 2

Preparation of N-methoxycarbonyl-phenothiazine-2-sulfonyl chloride

Method A

Dimethylformamide (0.23 g; 3 mmoles) and thionyl chloride (10 g; 84 mmoles) were added to a mixture of N-methoxycarbonyl-phenothiazine-2-sulfonic acid sodium salt (25 g; 62.5 mmoles, 90% titre), prepared as described in example 1, in methylene chloride (75 ml), under stirring at 15° C.

The mixture was heated under stirring and reflux for 4 hours, cooled to 20° C. and poured into water (100 ml). The phases were separated. The organic phase was dried on sodium sulfate and evaporated to dryness under vacuum obtaining N-methoxycarbonyl-phenothiazine-2-sulfonyl chloride (20.6 g; 58 mmoles; 92% yield).

A sample crystallized from toluene gave the pure compound.

$^1$H-NMR (300 MHz, CDCl$_3$): δ (ppm): 3.88 (s, 3H); 7.20–8.22 (m, 7H). m.p. 165°–167° C.

Mass spectrum (isobutane)=m/e 356 [M+H]+

Method B

Dimethylformamide (0.23 g; 3 mmoles) and thionyl chloride (10 g; 84 mmoles) were added to a mixture of N-methoxycarbonyl-phenothiazine-2-sulfonic acid sodium salt (25 g; 62.5 mmoles; 90% titre), prepared as described in example 1, in toluene (100 ml), under stirring at 150° C.

The mixture was heated at 60° C. for 4 hours and then poured into water (100 ml). The organic phase was separated at 60° C., azeotropically dried and cooled to 15° C. The precipitate was filtered and washed with diethyl ether (2×20 ml) obtaining N-methoxycarbonyl-phenothiazine-2-sulfonyl chloride (17.9 g; 50 mmoles).

The mother liquors contained further compound (3.4 g; 9.5 mmoles) (overall yield 96%).

The resultant compound had the same above reported analytic characteristics.

Method C

Chlorosulfonic acid (181.7 g; 1.56 moles) was added in about 30 minutes to a mixture of N-methoxycarbonyl-phenothiazine (200 g; 0.78 moles) in methylene chloride (240 ml) cooled at 15° C. under stirring and nitrogen.

The mixture was heated to 25° C. and kept at this temperature and under stirring fop 3 hours.

Then, the reaction mixture was poured into water cooled at 0° C. (600 g), the temperature was let arise up to the room value and the phases were separated.

N,N-dimethyl-n.octylamine (98.1 g; 0.62 moles) and methylene chloride (400 ml) were added to the aqueous phase under stirring.

After 30 minutes under stirring, the phases were separated and the organic phase was evaporated to dryness under vacuum.

Toluene (500 ml) was added to the resultant residue and the mixture was azeotropically dried.

After cooling at 60° C., dimethylformamide (4.1 g; 0.06 moles) and, in about 30 minutes, thionyl chloride (96.5 g; 0.81 moles) were added and the mixture was kept under stirring at 60° C. for 3 hours.

After cooling at 15° C. in 2 hours, the suspension was kept at 15° C. for 2 hours, the precipitate was filtered and washed with toluene (2×20 ml) obtaining N-methoxycarbonyl-phenothiazine-2-sulfonyl chloride (174 g; HPLC titre>97%; 60% yield from N-methoxycarbonyl-phenothiazine).

The compound had the same above reported analytic characteristics.

EXAMPLE 3

Preparation of N-methoxycarbonyl-2-mercapto-phenothiazine

Zinc (26.5 g; 0.405 g/atom) and, dropwise in 1 hour, 36% hydrochloric acid (116 g; 1.145 moles) were added to a mixture of N-methoxycarbonyl-phenothiazine-2-sulfonyl chloride (20.63 g; 0.058 moles), prepared as described in example 2, in methylene chloride cooled at 15° C. under nitrogen and stirring.

At the end of the addition, the mixture was heated under reflux for 4 hours.

After cooling at 20° C., the phases were separated, the organic phase was washed with 6N hydrochloric acid (50 ml), dried on sodium sulfate and evaporated to dryness.

N-methoxycarbonyl-2-mercapto-phenothiazine (15.9 g; 0.052 moles; 90% yield; 95% titre) was obtained.

An analytically pure sample was obtained by crystallization from ethyl acetate.

$^1$H-NMR (300 MHz, DMSO-d$_6$): δ (ppm): 3.74 (s, 3H); 5.80 (s, 1H); 7.17–7.61 (m, 7H) .

m.p. 145°–147° C.

EXAMPLE 4

Preparation of 2-mercapto-phenothiazine

Method A

A solution of sodium hydroxide (5.2 g; 0.13 moles) in water (47 ml) was heated to 70° C. and de-oxygenated with nitrogen for 30 minutes. Then, N-methoxycarbonyl-2-mercapto-phenothiazine (15.9 g; 0.052 moles; 95% titre), prepared as described in example 3, was added.

The mixture was heated under nitrogen for 4 hours at 70° C.

Then, charcoal (0.1 g) was added, the mixture was filtered, cooled at 15° C. and acidified up to pH 2 with hydrochloric acid (6N).

The precipitate was filtered and washed with water (2×20 ml) obtaining 2-mercapto-phenothiazine (11.2 g; 0.046 moles; 96% titre; 90% yield).

An analytically pure sample was obtained by crystallization from toluene.

m.p. 213°–215° C.

$^1$H-NMR (300 MHz, DMSO-d$_6$): δ (ppm): 5.39 (s, 1H); 6.60–7.01 (m, 1H); 8.58 (broad signal, 1H).

Method B

36% hydrochloric acid (54.5 g; 0.54 moles) was added to a mixture of N-methoxycarbonyl-phenothiazine-2-sulfonyl chloride (10 g; 0.028 moles), prepared as described in example 2, in toluene (35 ml), heated at 50° C. under nitrogen.

Zinc (12.8 g; 0.196 g/atom) was added portionwise and the mixture was heated at 50° C. for 4 hours.

The phases were separated. The organic phase contained N-methoxycarbonyl-2-mercapto-phenothiazine (7.5 g; 0.026 moles; 92% yield).

A solution of sodium hydroxide (2.6 g; 0.065 moles) in water (24 ml) was added under stirring to the organic phase. The mixture was heated at 80° C. for 3 hours under inert atmosphere. The phases were separated.

The aqueous phase, kept under inert atmosphere, was decolorized with charcoal (0.1 g) and filtered. 6N hydrochloric acid was added up to pH 2 and the suspension was cooled at 15° C. and filtered.

After drying under vacuum at 60° C., 2-mercapto-phenothiazine (5.75 g; 0.024 moles; HPLC titre 97%; 92% yield) with the same above reported analytic characteristics was obtained.

What we claim is:

1. A process for the preparation of 2-mercapto-phenothiazine by regioselective introduction in position 2 of an SH group, comprising:

reacting an N-protected phenothiazine of formula II

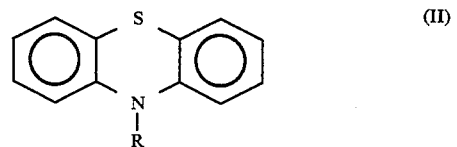

wherein R is a —COOR' or —SO$_2$R" group in which R' is a C$_1$–C$_6$ alkyl and R" is a C$_1$–C$_6$ alkyl or phenyl or naphthyl;

with a sulfonating agent selected from the group consisting of 96–98% sulfuric acid, sulfur trioxide, chlorosulfonic acid and oleum, in order to obtain a compound of formula III

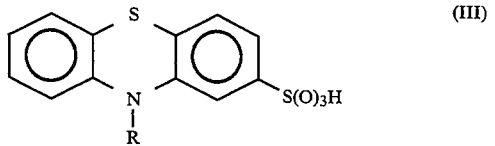

reducing the compound of formula III to obtain the N-protected 2-mercapto-phenothiazine of formula IV

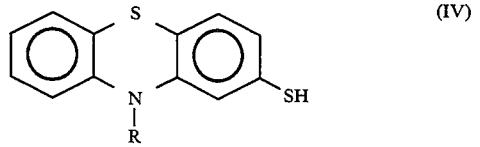

wherein R has the above reported meanings; and removing the protecting group from the nitrogen atom to obtain 2-mercapto-phenothiazine.

2. A process according to claim 1 wherein the sulfonating agent is chlorosulfonic acid.

3. A process according to claim 1 wherein R is a COOR' group.

4. A process according to claim 1 wherein the reducing step is carried out with zinc in an acid environment.

5. A process according to claim 1 in which the reduction step to compound (IV) is carried out onto the corresponding sulfonyl chloride derivative, obtained by reacting the compound of formula (III) with thionyl chloride.

* * * * *